United States Patent
Liphardt et al.

(10) Patent No.: US 9,658,151 B2
(45) Date of Patent: May 23, 2017

(54) SYSTEM FOR VIEWING SAMPLES THAT ARE UNDERGOING ELLIPSOMETRIC INVESTIGATION IN REAL TIME

(71) Applicants: Martin M. Liphardt, Lincoln, NE (US); Galen L. Pfeiffer, Roca, NE (US)

(72) Inventors: Martin M. Liphardt, Lincoln, NE (US); Galen L. Pfeiffer, Roca, NE (US)

(73) Assignee: J.A. WOOLLAM CO., INC., Lincoln, NE (US)

( * ) Notice: Subject to any disclaimer, the term of this patent is extended or adjusted under 35 U.S.C. 154(b) by 0 days.

(21) Appl. No.: 14/544,706

(22) Filed: Feb. 6, 2015

(65) Prior Publication Data

US 2015/0185136 A1    Jul. 2, 2015

Related U.S. Application Data

(63) Continuation-in-part of application No. 13/385,762, filed on Mar. 6, 2012, now Pat. No. 8,953,030.

(60) Provisional application No. 61/464,583, filed on Mar. 7, 2011.

(51) Int. Cl.
*G01N 21/21*   (2006.01)
*H04N 5/232*   (2006.01)
*G01N 21/55*   (2014.01)

(52) U.S. Cl.
CPC .......... *G01N 21/211* (2013.01); *G01N 21/55* (2013.01); *H04N 5/23212* (2013.01)

(58) Field of Classification Search
CPC ....................................................... H04N 7/18
See application file for complete search history.

(56) References Cited

U.S. PATENT DOCUMENTS

| | | | |
|---|---|---|---|
| 4,971,445 A * | 11/1990 | Sato et al. | G01B 11/24 250/559.22 |
| 5,120,966 A * | 6/1992 | Kondo | G01B 11/0616 250/372 |
| 5,517,312 A | 5/1996 | Finarov | |
| 5,963,326 A | 10/1999 | Masao | |
| 7,095,498 B2 * | 8/2006 | Horie | G01N 21/211 356/364 |
| 7,567,345 B1 * | 7/2009 | Liphardt | G01N 21/211 356/364 |

* cited by examiner

*Primary Examiner* — Dave Czekaj
*Assistant Examiner* — Berteau Joisil
(74) *Attorney, Agent, or Firm* — James D. Welch

(57) ABSTRACT

In the context of an ellipsometer or the like, positioning a camera other than directly above a sample being investigated by an electromagnetic beam, while said camera provides an optical view of a surface of said sample which is in focus over the entire viewed extent of the sample, and wherein a contrast improving system involving two beams provided by a beam splitting system is utilized.

6 Claims, 3 Drawing Sheets

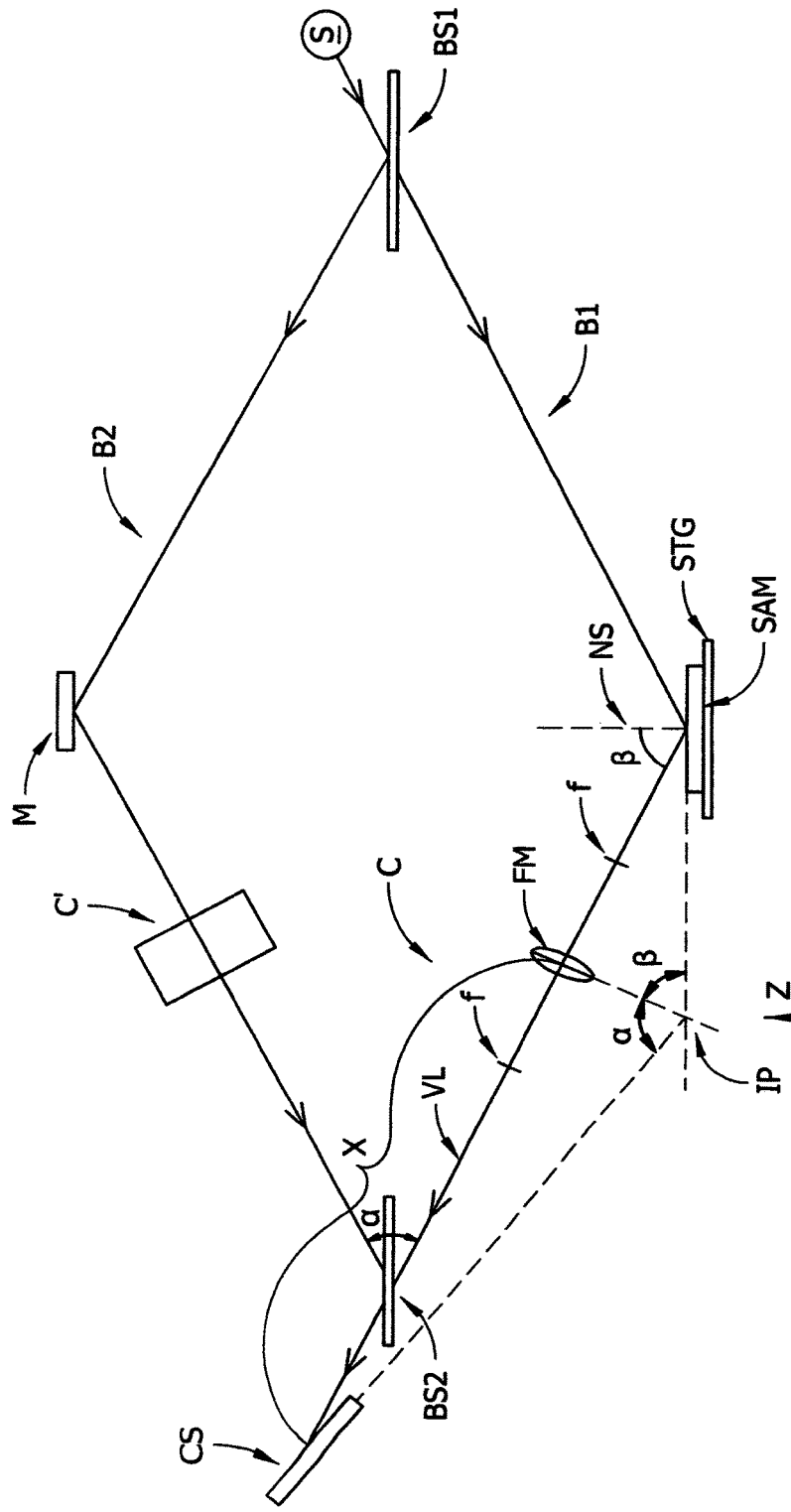
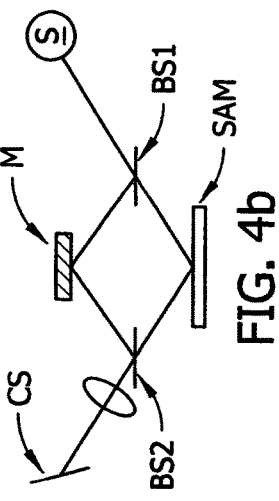
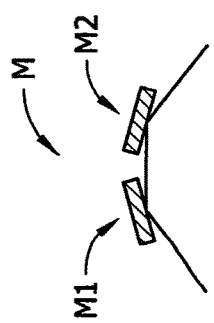
FIG. 4a
FIG. 4b
FIG. 4c

SYSTEM FOR VIEWING SAMPLES THAT ARE UNDERGOING ELLIPSOMETRIC INVESTIGATION IN REAL TIME

This application is a CIP of application Ser. No. 13/385,762; Filed Mar. 6, 2012 (now U.S. Pat. No. 8,953,030), and therevia Claims Benefit of Provisional Application 61/464,583 Filed Mar. 7, 2011.

TECHNICAL FIELD

The present invention relates to systems for investigating samples with electromagnetic beams, and more particularly to the positioning a camera other than directly above a sample being investigated, consistent with said camera providing an optical view of a surface of said sample which is in focus over the entire viewed extent of the sample.

BACKGROUND

It is known to position a sample such that an electromagnetic beam from a source thereof is caused to interact with said sample, and enter a detector. Change in intensity and/or polarization state of the beam is then analyzed to provide insight to the sample's optical and physical characteristics.

It is also known to place the source and detector on effective arms which operate on a 2θ basis, such that when the angle of incidence of a beam onto a sample is set at θ with respect to a perpendicular to the sample surface, the detector is also set at an angle θ, (reflected through the perpendicular locus), so that a beam reflecting from the sample enters thereinto. A problem can develop where the angles of incidence (AOI) and angle of reflection (AOR) both approach 0 degrees, (ie. both project near 0.0 degrees to a perpendicular to the sample surface), in that physical aspects of the effective arms, source and detector can limit motion. This is especially true when a camera, which is used to provide an optical view of sample during investigation by the electromagnetic beam, is positioned at an offset from the sample along a perpendicular to the surface thereof, as the camera is then often positioned so as to even further limit source and detector motion than otherwise is the case. Conventional thinking, however, is that such a camera must be positioned offset from a sample surface along a perpendicular thereto, as otherwise the image provided thereby will not be in focus over the full area of the sample.

Known prior art includes:

A Patent to Liphardt, U.S. Pat. No. 7,567,345 which describes applying a Scheimpflug condition to a source and/or detector in an ellipsometer system.

A Patent to Horie, U.S. Pat. No. 7,095,498 describes the presence of a pinhole mirror in a spectroscopic ellipsometer system. The pinhole mirror is rotated so that a beam of electromagnetic radiation is oriented along a locus which is oblique angle, rather than along a normal thereto;

A Patent to Masao, U.S. Pat. No. 5,963,326 describes an imaging ellipsometer which uses a large cross-section measuring beam rather than a small beam spot as is the focus in the present invention;

A Patent to Finarov, U.S. Pat. No. 5,517,312 mentions the Scheimpflug condition in the context of a scanning ellipsometer wherein a beam is scanned over a sample and a pattern recognition camera which is designed to utilize the Scheimpflug condition is applied;

The prior art does not, to the Inventor's knowledge, describe applying the Scheimpflug condition to design of reflectometer, ellipsometer, polarimeter or the like systems, where camera elements, which provide a view of the sample surface, are configured to meet the Scheimpflug condition.

DISCLOSURE OF THE INVENTION

As previously described in the Patent Application, the present invention recognizes the above identified problem and proposes that while physical limitations to achieving very small Angle-Of-Incidence (AOI) based on arm, source and detector dimensions can not be overcome by anything short of designing smaller system elements, it is possible to position a camera other than offset perpendicularly from a sample, and still achieve an image of the sample surface which is focused over the extent of its view. This is accomplished by providing a camera at a position other than directly above a sample surface and perpendicularly removed therefrom, combined with positioning a camera sensor plate which is tipped in a manner so that the "Scheimpflug condition", (see below), is met. Using this approach, it is possible to optically observe the surface of a sample with a camera oriented other than directly above a sample surface, with all viewed aspects thereof being in focus.

In its basic embodiment the present invention comprises and ellipsometer of the like comprising:
 a) a source of a beam of electromagnetic radiation;
 b) a stage for supporting a sample;
 c) a detector;
and further comprises:
 d) a camera comprising a camera sensor plate for viewing the surface of a sample placed on the stage for supporting a sample, as well as a focusing means.

To form an ellipsometer or polarimeter the system requires additional components such as polarization setting and monitoring elements, (eg. a polarizer, an analyzer and perhaps one or more compensators).

As mentioned, a present invention novel aspect is found in positioning and orientating camera sensor plate and focusing means elements such that the "Scheimpflug" condition is substantially met. To meet this condition in use, said camera sensor plate is caused to view a sample placed on a stage for supporting a sample, along an oblique viewpoint locus. Said oblique viewpoint locus (VL) is oriented at an angle Alpha (α) to said camera sensor plate, and projects substantially perpendicular to the plane of a focusing means, along the optical axis thereof. Further, said viewpoint locus "views" a surface of said sample placed on said stage for supporting a sample, along an oblique angle of incidence of Beta (β) with respect to a normal to a surface of said sample.

Novelty is found in the requirement that the camera sensor plate, focusing means and Ellipsometer or the like stage for supporting a sample are oriented with respect to one another such that a perpendicular to a projected plane of the camera sensor plate, a projected plane of the sample surface and a projected plane of the focusing means intersect, and such that the following condition is substantially met:

$$\mathrm{Tan}(\alpha) = (X-f)/f\, \mathrm{Tan}(\beta);$$

where Alpha (α) and Beta (β) were described above, and "X" is the distance from the camera sensor plate, at the point at which said camera view locus passed therethrough, to a center of said focusing means, and "f" is the focal length of said focusing means.

For clarity, it is to be understood that the terminology "plane of the camera sensor plate" refers to the orientation of a surface of the sensor plate, which is typically of a flat "sheet-like" construction. Further, to define the "plane" of the focusing means, consider that the focusing means can be considered to be a converging focusing lens with a relatively long longitudinal, and a relatively small/lateral dimension. The "plane" of said focusing lens is along the longitudinal dimension. Another way to express this condition is that the "plane" of the focusing means is perpendicular to the Optical axis thereof. This example should not be considered to limit the focusing means to being a converging focusing lens, and mathematical equivalents using reflective optics can also be applied within the scope of the present invention. The plane of the stage for supporting a sample refers to the orientation of the surface thereof.

The present invention then is a camera system for monitoring a surface of a sample, in functional combination with a reflectometer, ellipsometer, polarimeter or the like system: wherein said reflectometer, ellipsometer, polarimeter or the like system comprises:

a) a source of a beam of electromagnetic radiation;
    c) a stage for supporting a sample;
    d) a detector.

In use said source of a beam of electromagnetic radiation causes a beam of electromagnetic radiation to interact with a sample placed on said stage and reflect into said detector, such that sample characterizing data is produced thereby.

Said camera system for monitoring the surface of said sample comprises:

e) a camera sensor plate;
    f) a focusing means;

each of said camera sensor plate, focusing means and sample supporting stage each being oriented in identifiable planes, wherein:

the plane of the camera sensor plate refers to the orientation of its surface;
    the plane of the sample supporting stage refers to the orientation of its surface; and
    the plane of the focusing means is perpendicular to its optical axis.

In use, when said camera is positioned to observe a sample placed on said stage for supporting a sample along a camera viewpoint locus, said camera viewpoint locus forms an angle alpha ($\alpha$) with respect to the plane of said camera sensor plate, and proceeds from said camera sensor plate along a substantial perpendicular to the plane of said focusing means and along its optical axis, and such that said camera viewpoint locus further forms an oblique angle of incidence beta ($\beta$) with respect to a normal to a surface of said sample.

The Schiempflug condition provides that said camera sensor plate, focusing means and stage for supporting a sample be oriented with respect to one another such that a projected perpendicular to the plane of the camera sensor plate, a projected plane of the sample surface and a projected plane of the focusing means intersect, and such that the following condition is substantially met:

$$\operatorname{Tan}(\alpha) = (X-f)/f \operatorname{Tan}(\beta);$$

where "X" is the distance from the camera sensor plate, at the point at which said beam passes therethrough, to a center of said focusing means, and "f" is the focal length of said focusing means.

When the Schiempflug condition is met, the camera provides a focused view of the sample over the area thereof viewed.

A method of viewing a spot on a sample by a camera along an oblique viewpoint locus, wherein said spot is in focus over a substantial area of said spot comprises the steps of:

a) providing a combination reflectometer, reflectometer, ellipsometer or polarimeter and camera viewing system as just described; and
    b) adjusting the orientations of said camera sensor plate, focusing means and stage for supporting a sample with respect to one another such that a perpendicular to a projected plane of the camera sensor plate, a projected plane of the sample surface and a projected plane of the focusing means intersect at a common point, and such that the following condition is substantially met:

$$\operatorname{Tan}(\alpha) = (X-f)/f \operatorname{Tan}(\beta);$$

where Alpha ($\alpha$) is the angle between the viewpoint locus and the plane of the camera sensor plate, and Beta ($\beta$) is the angle between the viewpoint locus and a perpendicular to the plane of the sample surface.

ADDITIONAL DISCLOSURE

As described above, the present invention is a camera system for viewing, as opposed to providing a beam of electromagnetic radiation to conduct measurements on a surface of a sample, in functional combination with a reflectometer, ellipsometer, polarimeter or the like system. As recited before, said reflectometer, ellipsometer, polarimeter or the like system comprises:

a) an illuminating source of a beam of electromagnetic radiation;
    c) a stage for supporting a sample;
    d) a detector.

In use said illuminating source of a beam of electromagnetic radiation causes a beam of electromagnetic radiation to interact with a sample placed on said stage and reflect into said detector, such that sample characterizing data is produced thereby, said beam of electromagnetic radiation defining an "X"-"Z" plane in an orthogonal "X", "Y" and "Z" axis system.

Said camera system for monitoring the surface of said sample comprises:

e) a camera sensor plate;
    f) a focusor;

each of said camera sensor plate, focusor and sample supporting stage each being oriented in identifiable planes, wherein:

the plane of the camera sensor plate refers to the orientation of its surface;
    the plane of the sample supporting stage refers to the orientation of its surface; and
    the plane of the focusor is perpendicular to its optical axis.

In use when said camera is positioned to observe a sample placed on said stage for supporting a sample along a camera viewpoint locus (VL), said camera viewpoint locus forms an angle alpha ($\alpha$) with respect to the plane of said camera sensor plate, and proceeds from said camera sensor plate along a substantial perpendicular to the plane of said focusor and along its optical axis, and such that said camera viewpoint locus further forms an oblique angle of incidence beta ($\beta$) with respect to a normal to a surface of said sample, said camera being offset in both "Y", and "Z" directions from said "X"-"Z" plane.

Said camera sensor plate, focusor and stage for supporting a sample are oriented with respect to one another such that a projected perpendicular to the plane of the camera sensor plate, a projected plane of the sample surface and a projected plane of the focusor intersect at a common point, and such that the following condition is substantially met:

$$\operatorname{Tan}(\alpha) = (X-f)/f \operatorname{Tan}(\beta);$$

where "X" is the distance from the camera sensor plate, at the point at which said beam passes therethrough, to a center of said focusor, and "f" is the focal length of said focusor and where alpha (α) and beta (β) were defined above.

In use the camera provides a focused view of the sample over the area thereof viewed, while ellipsometric or the like data is acquired at small angles-of-incidence that are unattainable when the camera is present along the "Z" axis where it physically interferes with the positioning of said illuminating source of a beam of electromagnetic radiation and said detector.

Said system preferably further includes a contrast developing system comprising:
 a camera illumination source (S);
 a first beam splitter (BS1);
 at least one reflector (M);
 a compensating system (C');
 a second beam splitter (BS2).

In use said camera illuminating source (S) directs a beam of electromagnetic radiation at said first beam splitter (BS1), that in turn directs first (B1) and second (B2) beams of electromagnetic radiation exiting therefrom, the first (B1) reflecting from said sample (SAM), and the second beam (B2) at said at least one reflector (M) from which it reflects, such that said first (B1) and second (B2) beams reflected from said sample (SAM) and said at least one reflector (M) respectively, converge onto said second beam splitter (BS2) and interact with each other, to the end that a beam reflected from said second beam splitter (BS2) is directed onto said camera sensor plate (CS), such that said camera sensor plate (CS) is presented with an image forming beam of electromagnetic radiation that presents with increased contrast, as compared to that when said contrast developing system is not present.

There can further be present a compensating system (C') in the path of the second beam (B2) exiting said first beam splitter (BS1) that serves to at least partially compensate for elements in the path of said first beam (B1) exiting said first beam splitter (BS1), but are not otherwise present in the path of said second beam (B2) exiting said first beam splitter (BS1).

A method of viewing a sample surface in real time during investigation thereof by electromagnetic radiation, comprises the steps of:

a) providing a camera system (C) for viewing, as opposed to providing a beam (B) of electromagnetic radiation to conduct measurements on a surface of a sample (SAM), in functional combination with a reflectometer, ellipsometer, polarimeter or the like system (ES) as described just above, including said system further including a contrast developing system comprising:
 a first beam splitter (BS1);
 at least one reflector (M);
 a compensating system (C');
 a second beam splitter (BS2);

b) adjusting the orientations of the plane of at least one of said camera sensor plate (CS), sample (SAM) surface and focusor (FM) so that the Schiempflug condition is met thereby providing an in-focus view of the entire surface of said sample (SAM) while it is being investigated by electromagnetic radiation;

such that said camera sensor plate (CS) is presented with an image forming beam of electromagnetic radiation that presents with increased contrast, as compared to that when said contrast developing system is not present.

As mentioned before, said method can further include a compensating system (C') present in the path of the second beam (B2) exiting said first beam splitter (BS1) that serves to at least partially compensate for elements in the path of said first beam (B1) exiting said first beam splitter (BS1), but are not otherwise present in the path of said second beam (B2) exiting said first beam splitter (BS1).

Said system and method cn involve said camera being offset in the "X" direction as well as in the both "Y", and "Z" directions from said "X"-"Z" plane.

Said method can also involve using the reflectometer, ellipsometer, polarimeter or the like systems to acquire data by causing said source of a beam of electromagnetic radiation to provide a beam to said sample and monitoring output from said detector, and performing at least one selection from the group consisting of:
 storing at least some data provided by said data detector in machine readable media;
 analyzing at least some of the data provided by said data detector and storing at least some of the results of said analysis in machine readable media;
 displaying at least some data provided by said data detector by electronic and/or non-electronic means;
 analyzing at least some of the data provided by said data detector and displaying at least some of the results of said analysis by electronic and/or non-electronic means;
 causing at least some data provided by said data detector to produce a signal which is applied to provide a concrete and tangible result;
 analyzing at least some of the data provided by said data detector and causing at least some thereof to produce a signal which is applied to provide a concrete and tangible result.

The present invention will be better understood by reference to the Detailed description section of this Specification in conjunction with the Drawings.

BRIEF DESCRIPTION OF THE DRAWINGS

FIG. 1a shows an exemplary sample investigation system (ES) which uses an electromagnetic beam to investigate a sample (SAM) including conventional placement of a sample surface viewing camera (C).

FIG. 1b shows the "X", "Y" and "Z" axes that apply to FIG. 1a.

FIGS. 4a and 4b show a contrast developing system comprising a first beam splitter, a reflector, a compensating system and a second beam splitter.

FIG. 4c shows that there can be more than one reflector present in the contrast developing system.

DETAILED DESCRIPTION

Figures 1A, 1B:
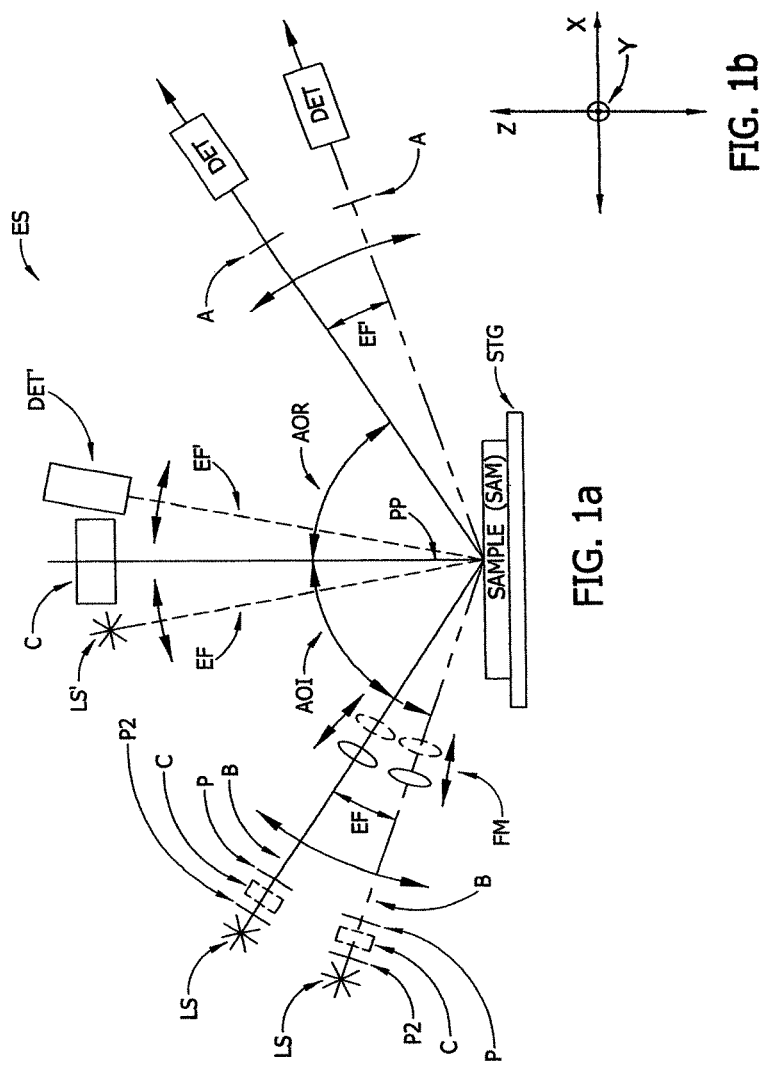

Turning now to FIG. 1a, there is shown, in the context of an indicated "X"-"Y"-"Z" axis system, (note the "Y" axis projects into the paper, the "Z" axis projects vertically and the "X" axis projects horizontally, as indicated in FIG. 1b), an exemplary Ellipsometer System (ES) oriented in an "X"-"Y" plane, and having a Source (LS) Electromagnetic Beam (B) and Detector (DET), each of which are mounted on Effective Arms (EA), that allow the (AOI) and (AOR) to be changed in a 2Ο manner. Also shown present is a Camera (C) removed from the Sample (SAM) along a perpendicular to its surface, (eg. along the "Z" axis), as is typical practice in order that the Camera (C) observe the Sample (SAM) surface in focus over its field of view. For insight, also shown are Ellipsometer elements including an Intensity Control Polarizer (P2), an Intensity Control Compensator (C), a Beam Polarizer (P), and Focusing Lens (FM) all functionally attached to said Effective Arm (EF), and an Analyzer (A) and Detector (DET) functionally attached to said Effective Arm (EF'). However, it is to be understood that the Present Invention can be practiced with no more than the Source (LS) functionally attached to Effective Arm (EF), a Sample (SAM) supporting stage, and a Detector (DET) functionally attached to Effective Arm (EF'), where only Beam Intensity change resulting from interaction with the Sample (SAM) is of interest.

Importantly, it should be apparent that the Effective Arm (EF) to which the Source (LS) of a Beam (B) of electromagnetic radiation is attached, as shown in FIG. 1a, can only rotate so far clockwise without it, or the Source (LS) bumping into the Camera (C), and that the Effective Arm (EF') to which the Detector (DET) is attached can only rotate so far counter-clockwise without it, or the Detector (DET'), bumping into the Camera (C). Present practice utilizing a camera (C) therefore limits achieving very small EM Beam (B) Angles-of-Incidence (AOI) and Reflection (AOR). Utility would therefore be provided by positioning the Camera (C) otherwise than as shown in FIG. 1a.

The present invention breaks with the FIG. 1a convention by placing the Camera (C) out of the way, (ie. so that the Camera (C) does not interfere with the clockwise and counter-clockwise motions of the respective Effective Arms (EA) (EA') that include the Source of an EM Beam (LS) and Detector (DET), respectively).

Figure 2:
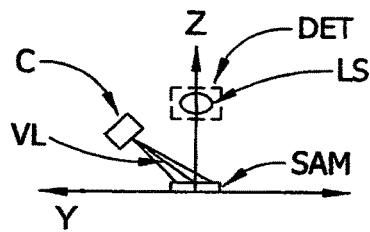
FIG. 2 demonstrates relative positioning of a camera (C) in the system of FIG. 1 which removes it from a position in which it interferes with movement of effective arms (EF) and (EF').

FIG. 2 shows the Present Invention positioning of the Camera (C) which can be thought of, for instance, as a location arrived at by moving the Camera (C) in a -Y direction into the paper "Y"-"Z" plane, to position the Camera (C) as shown in FIG. 2. However, this example is not limiting. It is important to realize that the Camera (C) can be placed essentially anywhere that allows it to have an oblique view of the Sample (SAM) surface being investigated by the Ellipsometer or the like EM Beam. FIG. 2 also identifies a Camera Viewpoint Locus (VL).

Figure 3:
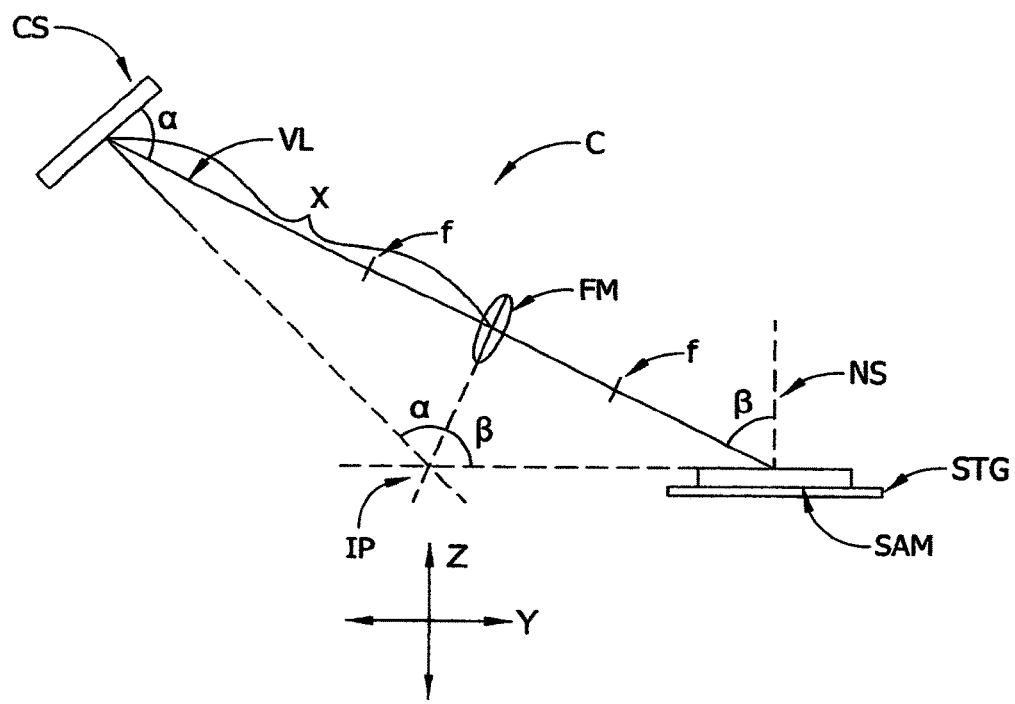
FIG. 3 shows the camera positioned as in FIG. 2, wherein a sensor plate and focusing means, (eg. lens), and a sample can be arranged to meet a mathematical relationship defined by the "Scheimpflug" condition.

FIG. 3 demonstrates the Sheimpflug condition applied to the Camera (C), which when met allows said Camera (C), when positioned, for instance, as demonstrated in FIG. 2, to observe the entire viewed Sample (SAM) surface—in focus—, even though some portions of the Sample (SAM) are, from the Camera's viewpoint, closer thereto, and some portions of the Sample (SAM) are, from the Camera's viewpoint, further therefrom. FIG. 3 shows relative positioning and orientation of the Camera's viewpoint locus (VL), a Sample (SM) placed on the Ellipsometer or the like Stage (STG) for supporting a Sample, a Camera Sensor Plate (CS) and a Focusing Means (FM), (eg. lens), and indicates angels Alpha (α) and Beta (β). When the identified elements are properly oriented with respect to one another, a mathematical relationship defined by the "Scheimpflug" condition results. In particular, Alpha (α) is the angle between the Viewpoint Locus (VL) and the plane of the Camera Sensor Plate (CS), and Beta (β) is the oblique angle between said Viewpoint Locus (VL) and a normal to the plane of the Sample (SAM). The Equation shown is the defining equation for the Scheimpflug condition:

$$\text{Tan}(\alpha) = (X-f)/f \text{ Tan}(\beta);$$

where "X" is the distance from the camera sensor plate (CS), at the point at which said camera viewpoint locus (VL) passes therethrough, to a center of said focusing means, and "f" is the focal length of said focusing means. Again, Alpha (α) is the angle between the plane of the Camera Sensor Plate (CS) and the Viewpoint Locus (VL), and Beta (β) is the oblique angle of incidence the beam (B1) makes with a normal (NS) to the Sample (SAM) surface. Note that projected planes of the Focusing Means (FM) and Sample (SAM), and a perpendicular to the Camera Sensor Plate (CS) intersect at Intersection Point (IP) when the Scheimpflug condition is met. When the various elements are oriented as described, the Camera (C) will have a focused view of the viewed area of the Sample (SAM) being viewed thereby.

It is application of the Scheimpflug condition to a Camera (C) viewpoint locus (VL) positioned, for instance, in the "Y"-"Z" plane, as shown in FIG. 2, to allow a view of the entire surface of Sample (SAM) in focus, while allowing the associated Ellipsometer System (ES) to achieve the smallest (AOI) and (AOR) possible for the Ellipsometer System (ES) being applied, unaffected by Camera (C) presence imposed limitations, as indicated by FIG. 1a, which is the focal point of the present invention.

Again, as it is important, the FIG. 2 demonstration of the positioning of the Camera (C) is not limiting. The Camera can be positioned essentially anywhere that it does not interfere with movement of the Effective Arms (EF) (EF'), but also allows the Camera (C) an oblique view of the Sample (SAM) surface being investigated by the EM Beam (B). Of course the various elements of the system will then require appropriate relative orientations for different Camera (C) positioning, to satisfy the Scheimpflug condition.

It is noted that while the Camera Sensor Plate (CS) and Focusing Means (FM) are not shown as encompassed within a camera housing, while not absolutely necessary, it is common practice that they are so housed.

FIGS. 4a and 4b show a contrast developing system comprising a first beam splitter, at least one reflector (M), a compensating system and a second beam splitter which is added to the previously described system. In more detail said system further includes however, a contrast developing system comprising:

a first beam splitter (BS1);
at least one reflector (M);
a compensating system (C');
a second beam splitter (BS2);

such that in use said camera illuminating source (S) directs a beam of electromagnetic radiation at said first beam splitter (BS1), that in turn directs first (B1) and second (B2) beams of electromagnetic radiation exiting therefrom, the first (B1) reflecting from said sample (SAM), and the second beam (B2) at said at least one reflector (M) from which it reflects, such that said first (B1) and second (B2) beams reflected from said sample (SAM) and said at least one reflector (M) respectively, converge onto said second beam splitter (BS2) and interact with each other, to the end that a beam reflected from said second beam splitter (BS2) is directed onto said camera sensor plate (CS), such that said camera sensor plate (CS) is presented with an image forming beam of electromagnetic radiation that presents with increased contrast, as compared to that when said contrast developing system is not present.

FIG. 4c is included to show that there can be more than one reflector (M1) (M2) present in the contrast developing system. Said combination is collectively considered as the reflector (M) in FIGS. 4a and 4b. There can be three or more reflectors as well.

Having hereby disclosed the subject, matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A camera system (C) for viewing, as opposed to providing a beam (B) of electromagnetic radiation to conduct measurements on a surface of a sample (SAM), in functional combination with a reflectometer, ellipsometer, polarimeter or the like system (ES):

wherein said reflectometer, ellipsometer, polarimeter or the like system (ES) comprises:
   a) an illuminating source (LS) of a beam of electromagnetic radiation;
   c) a stage (STG) for supporting a sample;
   d) a detector (DET);
such that in use said illuminating source (LS) of a beam of electromagnetic radiation causes a beam of electromagnetic radiation to interact with a sample (SAM) placed on said stage (STG) and reflect into said detector (DET), such that sample characterizing data is produced thereby, said beam of electromagnetic radiation defining an "X"-"Z" plane in an orthogonal "X", "Y" and "Z" axis system;
and said camera system (C) for monitoring the surface of said sample comprises:
   e) a camera sensor plate (CS);
   f) a focusor (FM);
each of said camera sensor plate (CS), focusor (FM) and sample supporting stage (STG) each being oriented in identifiable planes, wherein:
   the plane of the camera sensor plate (CS) refers to the orientation of its surface;
   the plane of the sample supporting stage (STG) refers to the orientation of its surface; and
   the plane of the focusor (FM) is perpendicular to its optical axis;
such that in use when said camera (C) is positioned to observe a sample placed on said stage for supporting a sample along a camera viewpoint locus (VL), said camera viewpoint locus forms an angle alpha ( ) with respect to the plane of said camera sensor plate, and proceeds from said camera sensor plate along a substantial perpendicular to the plane of said focusor and along its optical axis, and such that said camera viewpoint locus further forms an oblique angle of incidence beta ( ) with respect to a normal to a surface of said sample, said camera being offset in both "Y", and "Z" directions from said "X"-"Z" plane;
said camera sensor plate (CS), focusor (FM) and stage (STG) for supporting a sample (SAM) being oriented with respect to one another such that a projected perpendicular to the plane of the camera sensor plate, a projected plane of the sample (SAM) surface and a projected plane of the focusor (FM) intersect at a common point, and such that the following condition is substantially met:

$$\mathrm{Tan}(\alpha) = (X-f)/f\,\mathrm{Tan}(\beta);$$

where "X" is the distance from the camera sensor plate (CS), at the point at which said beam passes therethrough, to a center of said focusor (FM), and "f" is the focal length of said focusor (FM) and where alpha ($\alpha$) and beta ($\beta$) were defined above;

such that, in use the camera (C) provides a focused view of the sample (SAM) over the area thereof viewed, while ellipsometric or the like data is acquired at small angles-of-incidence that are unatainable when the camera is present along the "Z" axis where it physically interferes with the positioning of said illuminating source (SAM) of a beam of electromagnetic radiation and said detector;

said system further including a contrast developing system comprising:
   a camera illumination source (S);
   a first beam splitter (BS1);
   at least one reflector (M);
   a compensating system (C');
   a second beam splitter (BS2);
such that in use said camera illuminating source (S) directs a beam of electromagnetic radiation at said first beam splitter (BS1), that in turn directs first (B1) and second (B2) beams of electromagnetic radiation exiting therefrom, the first (B1) reflecting from said sample (SAM), and the second beam (B2) at said at least one reflector (M) from which it reflects, such that said first (B1) and second (B2) beams reflected from said sample (SAM) and said at least one reflector (M) respectively, converge onto said second beam splitter (BS2) and interact with each other, to the end that a beam reflected from said second beam splitter (BS2) is directed onto said camera sensor plate (CS), such that said camera sensor plate (CS) is presented with an image forming beam of electromagnetic radiation that presents with increased contrast, as compared to that when said contrast developing system is not present.

2. A system as in claim 1, in which there is further a compensating system (C') in the path of the second beam (B2) exiting said first beam splitter (S1) that serves to at least partially compensate for elements in the path of said first beam (B1) exiting said first beam splitter (BS1), but are not otherwise present in the path of said second beam (BS2) exiting said first beam splitter (BS1).

3. A method of viewing a sample surface in real time during investigation thereof by electromagnetic radiation, comprising the steps of:
providing a reflectometer, ellipsometer, polarimeter or the like system (ES) which comprises:
   a) an illuminating source (LS) of a beam of electromagnetic radiation;
   c) a stage (STG) for supporting a sample;
   d) a detector (DET);
such that in use said illuminating source (LS) of a beam of electromagnetic radiation causes a beam of electromagnetic radiation to interact with a sample (SAM) placed on said stage (STG) and reflect into said detector (DET), such that sample characterizing data is produced thereby, said beam of electromagnetic radiation defining an "X"-"Z" plane in an orthogonal "X", "Y" and "Z" axis system;
and said camera system (C) for monitoring the surface of said sample comprises:
   e) a camera sensor plate (CS);
   f) a focusor (FM);
each of said camera sensor plate (CS), focusor (FM) and sample supporting stage (STG) each being oriented in identifiable planes, wherein:

the plane of the camera sensor plate (CS) refers to the orientation of its surface;

the plane of the sample supporting stage (STG) refers to the orientation of its surface; and the plane of the focusor (FM) is perpendicular to its optical axis;

such that in use when said camera (C) is positioned to observe a sample placed on said stage for supporting a sample along a camera viewpoint locus (VL), said camera viewpoint locus forms an angle alpha ($\alpha$) with respect to the plane of said camera sensor plate, and proceeds from said camera sensor plate along a substantial perpendicular to the plane of said focusor and along its optical axis, and such that said camera viewpoint locus further forms an oblique angle of incidence beta ($\beta$) with respect to a normal to a surface of said sample, said camera being offset in both "Y", and "Z" directions from said "X"-"Z" plane;

said camera sensor plate (CS), focusor (FM) and stage (STG) for supporting a sample (SAM) being oriented with respect to one another such that a projected perpendicular to the plane of the camera sensor plate, a projected plane of the sample (SAM) surface and a projected plane of the focusor (FM) intersect at a common point, and such that the following condition is substantially met:

$$\mathrm{Tan}(\alpha) = (X-f)/f\,\mathrm{Tan}(\beta);$$

where "X" is the distance from the camera sensor plate (CS), at the point at which said beam passes therethrough, to a center of said focusor (FM), and "f" is the focal length of said focusor (FM) and where alpha ($\alpha$) and beta ($\beta$) were defined above;

such that, in use the camera (C) provides a focused view of the sample (SAM) over the area thereof viewed, while ellipsometric or the like data is acquired at small angles-of-incidence that are unatainable when the camera is present along the "Z" axis where it physically interfere with the positioning of said illuminating source (SAM) of a beam of electromagnetic radiation and said detector;

said system further including a contrast developing system comprising:
  a camera illumination source (S);
  a first beam splitter (BS1);
  at least one reflector (M);
  a compensating system (C');
  a second beam splitter (BS2);

such that in use said camera illuminating source (S) directs a beam of electromagnetic radiation at said first beam splitter (BS1), that in turn directs first (B1) and second (B2) beams of electromagnetic radiation exiting therefrom, the first (B1) reflecting from said sample (SAM), and the second beam (B2) at said at least one reflector (M) from which it reflects, such that said first (B1) and second (B2) beams reflected from said sample (SAM) and said at least one reflector (M) respectively, converge onto said second beam splitter (BS2) and interact with each other, to the end that a beam reflected from said second beam splitter (BS2) is directed onto said camera sensor plate (CS), such that said camera sensor plate (CS) is presented with an image forming beam of electromagnetic radiation that presents with increased contrast, as compared to that when said contrast developing system is not present;

b) adjusting the orientations of the plane of at least one of said camera sensor plate (CS), sample (SAM) surface and focusor (FM) so that the Schiempflug condition is met thereby providing an in-focus view of the entire surface of said sample (SAM) while it is being investigated by electromagnetic radiation;

such that said camera sensor plate (CS) is presented with an image forming beam of electromagnetic radiation that presents with increased contrast, as compared to that when said contrast developing system is not present.

4. A method as in claim 3, in which there is further a compensating system (C') in the path of the second beam (B2) exiting said first beam splitter (BS1) that serves to at least partially compensate for elements in the path of said first beam (B1) exiting said first beam splitter (BS1), but are not otherwise present in the path of said second beam (B2) exiting said first beam splitter (BS1).

5. A system as in claim 1 in which said camera is offset in the "X" direction as well as in the both "Y", and "Z" directions from said "X"-"Z" plane.

6. A method as in claim 3 in which said camera is offset in the "X" direction as well as in the both "Y", and "Z" directions from said "X"-"Z" plane.

* * * * *